US00PP21208P2

(12) United States Plant Patent
Lemon

(10) Patent No.: US PP21,208 P2
(45) Date of Patent: Aug. 17, 2010

(54) ***GERANIUM* PLANT NAMED 'OGLGER11142'**

(50) Latin Name: *Pelargonium×hortorum*
Varietal Denomination: Oglger11142

(75) Inventor: David Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 16 days.

(21) Appl. No.: 12/316,456

(22) Filed: Dec. 12, 2008

(51) Int. Cl.
*A01H 5/00* (2006.01)

(52) U.S. Cl. ..... Plt./329

(58) Field of Classification Search ..... Plt./329
See application file for complete search history.

(56) References Cited

U.S. PATENT DOCUMENTS

PP7,623 P * 8/1991 Meilland ..... Plt./137
PP8,969 P * 11/1994 Bradford et al. ..... Plt./185
PP12,274 P2 * 12/2001 Utecht ..... Plt./329

* cited by examiner

*Primary Examiner*—Wendy C. Haas
(74) *Attorney, Agent, or Firm*—C.A. Whealy

(57) ABSTRACT

A new and distinct cultivar of Zonal *Geranium* plant named 'Oglger11142', characterized by its upright, outwardly spreading and mounded plant habit; freely branching habit; freely and early flowering habit; red purple-colored flowers with a red-colored central splash; and good garden performance.

1 Drawing Sheet

Botanical designation: *Pelargonium×hortorum*.
Cultivar denomination: 'Oglger11142'.

BACKGROUND OF THE INVENTION

The present invention relates to a new and distinct cultivar of Zonal *Geranium* plant, botanically known as *Pelargonium×hortorum*, and hereinafter referred to by the name 'Oglger11142'.

The new Zonal *Geranium* plant is a product of a planned breeding program conducted by the Inventor in Lompoc, Calif. The objective of the breeding program is to create new vigorous Zonal *Geranium* cultivars with dark green-colored foliage and attractive flower coloration.

The new Zonal *Geranium* plant originated from a cross-pollination made by the Inventor in May, 2000 in Lompoc, Calif. of a proprietary selection of *Pelargonium×hortorum* identified as code number 8969,not patented, as the female, or seed, parent with a proprietary selection of *Pelargonium×hortorum* identified as code number 7623, not patented, as the male, or pollen, parent. The new Zonal *Geranium* was discovered and selected by the Inventor as a single flowering plant from within the progeny of the stated cross-pollination in a controlled greenhouse environment in Lompoc, Calif. in January, 2001.

Asexual reproduction of the new Zonal *Geranium* plant by vegetative terminal cuttings in a controlled greenhouse environment in Connellsville, Pa. since April, 2001, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Oglger11142'. These characteristics in combination distinguish 'Oglger11142' as a new and distinct cultivar of Zonal *Geranium*:

1. Upright, outwardly spreading and mounded plant habit.
2. Freely branching habit.
3. Freely and early flowering habit.
4. Red purple-colored flowers with a red-colored central splash.
5. Good garden performance.

Plants of the new Zonal *Geranium* differ from plants of the female parent selection primarily in flower color as plants of the female parent selection have pink-colored flowers.

Plants of the new Zonal *Geranium* differ from plants of the male parent selection primarily in leaf and flower color as plants of the male parent selection have lighter green-colored leaves and purple-colored flowers.

Plants of the new Zonal *Geranium* can be compared to plants of *Pelargonium×hortorum* 'Fistangoli', disclosed in U.S. Plant Pat. No. 12,274. In side-by-side comparisons conducted in Connellsville, Pa., plants of the new Zonal *Geranium* differed from plants of 'Fistangoli' primarily in flower color as plants of 'Fistangoli' had less intense red purple-colored flowers.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*.

The photograph comprises a side perspective view of a typical flowering plant of 'Oglger11142' grown in a container.

DETAILED BOTANICAL DESCRIPTION

The aforementioned photograph and following observations, measurements and values describe plants grown in Connellsville, Pa. in a glass-covered greenhouse during the summer and under conditions which closely approximate Zonal *Geranium* commercial production. During the production of the plants, day temperatures ranged from 21° C. to 32° C., night temperatures ranged from 17° C. to 21° C. and light levels ranged from 2,500 to 3,000 foot-candles. Plants had been growing for nine weeks when the photograph and the description were taken. In the following detailed description, color references are made to The Royal Horticultural Society Colour Chart, 2001 Edition, except where general terms of ordinary dictionary significance are used.

Botanical classification: *Pelargonium×hortorum* 'Oglger11142'.

Parentage:

*Female, or seed, parent.*—Proprietary selection of *Pelargonium×hortorum* identified as code number 8969, not patented. Male, or pollen, parent: Proprietary selection of *Pelargonium×hortorum* identified as code number 7623, not patented.

Propagation:

*Type.*—By vegetative terminal cuttings.

*Time to initiate roots, summer:.*—About ten days at temperatures of 20° C.

*Time to initiate roots, winter.*—About two weeks at temperatures of 16° C.

*Time to produce a rooted young plant, summer.*—About four weeks at temperatures of 20° C.

*Time to produce a rooted young plant, winter.*—About four weeks at temperatures of 16° C.

*Root description.*—Fine, fibrous; white in color.

*Rooting habit.*—Freely branching.

Plant description:

*General appearance.*—Upright and outwardly spreading plant habit; uniformly mounded; densely foliated.

*Growth and branching habit.*—Moderately vigorous growth habit. Freely branching habit.

*Plant height, to top of foliar plane.*—About 9.9 cm to 13.5 cm.

*Plant height, to top of umbels.*—About 23.8 cm to 25.5 cm.

*Plant width.*—About 26.6 cm to 27.5 cm.

*Main stems.*—Length: About 7.5 cm to 9.3 cm. Diameter: About 8 mm to 10 mm. Internode length: About 5 mm to 15 mm. Texture: Pubescent. Strength: Strong. Color: Close to 143C.

*Primary lateral branches.*—Length: About 1.7 cm to 2.5 cm. Diameter: About 9 mm to 11 mm. Internode length: About 1.2 cm to 1.5 cm. Texture: Slightly to moderately pubescent. Strength: Strong. Color: Close to 144B.

Foliage description:

*Arrangement.*—Alternate, simple.

*Length.*—About 6.5 cm to 7.1 cm.

*Width.*—About 7.7 cm to 8.4 cm.

*Shape.*—Reniform.

*Apex.*—Rounded.

*Base.*—Cordate.

*Margin.*—Crenate.

*Venation pattern.*—Palmate.

*Texture, upper and lower surfaces.*—Pubescent; velvety.

*Color.*—Developing foliage, upper surface: Close to 141B. Developing foliage, lower surface: Close to 141C. Fully expanded foliage, upper surface: Close to 141B; venation, close to 143C. Fully expanded foliage, lower surface: Close to 144B; venation, close to 143C. Zonation pattern: Not observed.

*Petiole.*—Length: About 6.1 cm to 7.7 cm. Diameter: About 3 mm to 4 mm. Texture, upper and lower surfaces: Smooth, glabrous. Color, upper and lower surfaces: Close to 143A.

Flower description:

*Flower arrangement.*—Rotate flowers arranged in rounded hemispherical umbels arising from apical leaf axils. Umbels displayed above the foliage on strong peduncles. Flowers face upright to outward; flowers slightly cupped becoming flatter with development.

*Fragrance.*—None detected.

*Quantity of flowers.*—Freely flowering habit; about 12 to 20 flowers per umbel and about two to three umbels per lateral branch.

*Flowering season.*—In Connellsville, Pa., flowering is continuous during the spring and summer.

*Flower longevity.*—Individual flowers last about 10 to 14 days on the plant; flowers not persistent.

*Umbel height.*—About 4.5 cm to 4.8 cm.

*Umbel diameter.*—About 7.7 cm to 9.5 cm.

*Flower diameter.*—About 3.6 cm to 4.1 cm.

*Flower depth* (*height*).—About 9 mm to 16 mm.

*Flower buds.*—Length: About 6 mm to 12 mm Diameter: About 5 mm to 7 mm. Shape: Elliptical.

*Petals.*—Quantity per flower: About six to nine. Length: About 1.9 cm to 2.2 cm. Width: About 1.8 cm to 2 cm. Shape: Roughly spatulate. Apex: Rounded. Base: Attenuate. Margin: Entire. Texture, upper and lower surfaces: Smooth, glabrous. Color: When opening and fully opened, upper two petals, upper surface: Towards the apex, close to 61B, central splash, close to 44C; towards the base, close to N155B. When opening and fully opened, lower three petals, upper surface: Close to N66A to N66B; towards the base, close to N155B. When opening and fully opened, upper two petals, lower surface: Close to 67A; towards the base, close to 41A; at the base, close to N155B; venation, close to 45D. When opening and fully opened, lower three petals, lower surface: Close to 67A; towards the base, close to 47C; at the base, close to N155B; venation, close to N155B.

*Petaloids.*—Quantity per flower: About one to three. Length: About 1.3 cm to 1.7 cm. Width: About 6 mm to 8 mm. Shape: Irregular. Apex: Rounded. Base: Attenuate. Margin: Entire. Texture, upper and lower surfaces: Smooth, glabrous. Color: When opening and fully opened, upper surface: Close to N66A. When opening and fully opened, lower surface: Close to N66B.

*Sepals.*—Quantity per flower: Five, arranged in a single whorl. Length: About 2 cm. Width: About 5 mm. Shape: Lanceolate. Apex: Acute. Base: Attenuate. Margin: Entire. Color, upper and lower surfaces: Close to 144A.

*Peduncle* (*umbel stem*).—Length: About 13.6 cm to 14.4 cm. Diameter: About 3.5 mm to 4 mm. Strength: Strong. Texture: Moderately pubescent. Color: Close to N199D.

*Pedicel* (*individual flower stem*).—Length: About 2.1 cm to 3.8 cm. Diameter: About 1.5 mm to 2 mm. Strength: Moderately strong. Texture: Pubescent. Color: Close to N199D.

*Reproductive organs.*—Androecium: Stamen quantity per flower: About five to eight. Filament length: About 5 mm to 7 mm. Filament color: Close to N155B. Anther length: About 2 mm to 3 mm. Anther shape: Oval. Anther color: Close to 47C. Pollen amount: Abundant. Pollen color: Close to 168B. Gynoecium: Pistil quantity per flower: One. Pistil length: About 9 mm. Stigma shape: Split into five parts. Stigma size: About 2 mm. Stigma color: Close to 50A. Style length: About 2 mm. Style color: Close to 51B. Ovary color: Slightly darker than 139D.

*Seed.*—Seed development has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 1° C. to about 35° C. and have demonstrated good garden performance.

It is claimed:

1. A new and distinct Zonal *Geranium* plant named 'Oglger11142' as illustrated and described.

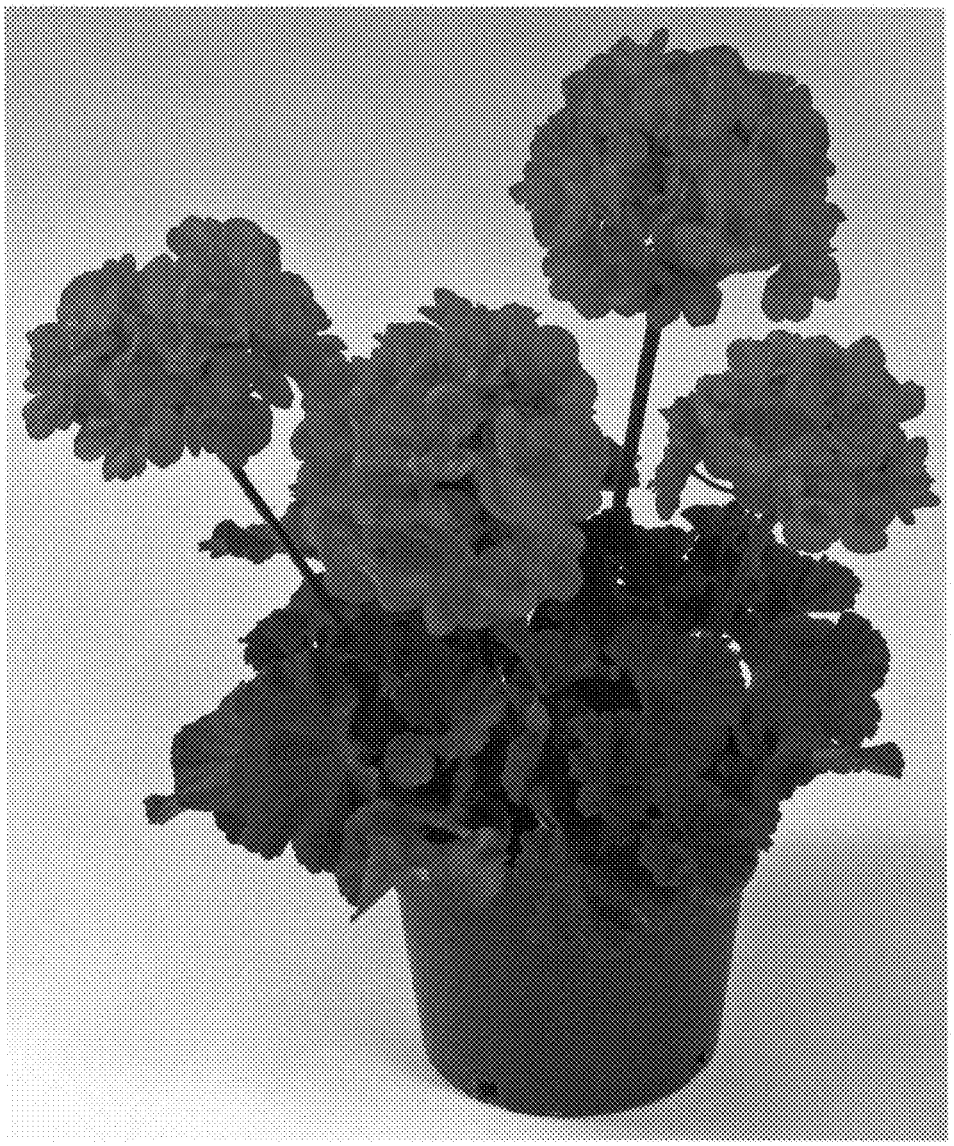

* * * * *